US012770719B2

(12) United States Patent
Payling et al.

(10) Patent No.: US 12,770,719 B2
(45) Date of Patent: Oct. 20, 2026

(54) MEDICAL TREATMENT SELECTOR

(71) Applicant: C The Signs Limited, London (GB)

(72) Inventors: Miles Payling, London (GB); Bhavagaya Bakshi, London (GB)

(73) Assignee: C The Signs Limited, London (GB)

( * ) Notice: Subject to any disclaimer, the term of this patent is extended or adjusted under 35 U.S.C. 154(b) by 0 days.

(21) Appl. No.: 18/885,211

(22) Filed: Sep. 13, 2024

(65) Prior Publication Data

US 2026/0004894 A1 Jan. 1, 2026

(30) Foreign Application Priority Data

Jun. 28, 2024 (GB) ..................................... 2409375
Aug. 21, 2024 (EP) ..................................... 24195744

(51) Int. Cl.
*G16H 20/00* (2018.01)
*G16H 10/20* (2018.01)
*G16H 10/60* (2018.01)
*G16H 50/70* (2018.01)

(52) U.S. Cl.
CPC ............ *G16H 10/20* (2018.01); *G16H 10/60* (2018.01); *G16H 20/00* (2018.01); *G16H 50/70* (2018.01)

(58) Field of Classification Search
None
See application file for complete search history.

(56) References Cited

U.S. PATENT DOCUMENTS 12,002,553 B2 6/2024 Ennist et al.
2006/0265253 A1* 11/2006 Rao ........................ G16H 70/20 705/3
2012/0316898 A1* 12/2012 Levitt .................... G16H 10/20 705/3
2013/0332191 A1* 12/2013 Hoffman ................ G06Q 30/02 705/3

(Continued)

FOREIGN PATENT DOCUMENTS

WO WO-2006125097 A2 * 11/2006 ............. G16H 10/60

OTHER PUBLICATIONS

"Clinical Trial Basics: Pre-Screening and Screening"; WithPower.com; May 10, 2023 (Year: 2023).*

(Continued)

*Primary Examiner* — John A Pauls
(74) *Attorney, Agent, or Firm* — Wolf, Greenfield & Sacks, P.C.

(57) ABSTRACT

The disclosure provides a computer-implemented method of determining a medical treatment for a patient. The method comprises: obtaining a patient data set; applying a set of eligibility criteria to patient values to determine whether the patient is eligible for the medical treatment; obtaining further patient values and reapplying the eligibility criteria; obtaining, in response to a determination that a status of diagnosis data in the medical records system has changed, an indication of a diagnosis of a medical condition for the patient; and, in response to the indication that the patient has been diagnosed with the medical condition, and that the patient is eligible for the medical treatment, providing, through a user interface layer or through a network interface connection, an output signal to direct a clinician to provide the patient with the medical treatment.

18 Claims, 5 Drawing Sheets

(56) References Cited

U.S. PATENT DOCUMENTS

| | | | | |
|---|---|---|---|---|
| 2014/0194353 | A1* | 7/2014 | Kahn | A61K 38/28<br>435/7.1 |
| 2016/0196411 | A1* | 7/2016 | Zhang | H04L 63/102<br>705/2 |
| 2020/0258600 | A1* | 8/2020 | Will | G06N 3/0442 |
| 2020/0381087 | A1* | 12/2020 | Ozeran | G06F 16/31 |
| 2022/0084633 | A1 | 3/2022 | Das et al. | |
| 2022/0180979 | A1* | 6/2022 | Brooks | G16H 50/70 |

OTHER PUBLICATIONS

Extended European Search Report for Application No. 24195744.8-1122, dated Feb. 26, 2025, 10 pages.

* cited by examiner

500

MEDICAL TREATMENT SELECTOR

CROSS-REFERENCE TO RELATED APPLICATIONS

This application claims priority to, and the benefit of, GB 2409375.9, filed 28 Jun. 2024, and EP 24195744.8, filed 21 Aug. 2024, the disclosures of which are expressly incorporated herein by reference in their entireties.

TECHNICAL FIELD

The present disclosure relates to systems and methods for selecting medical treatments for a patient, for example methods for determining the eligibility of patients to participate in a clinical trial.

BACKGROUND

The typical timeline for a patient, between presenting with the symptoms of a disease through to diagnosis and treatment can be drawn out into many different stages, with each potentially involving different clinicians. Similarly, the process by which a patient may be determined to be eligible for a particular clinical trial can also be drawn out along this timeline, with patients often only identified as being eligible for a trial long after they are diagnosed with a condition, and often long after specialist hospital treatments have started, which in turn can impact their eligibility. In many cases, patients are only identified as eligible after a second- or third-line treatment for the condition has been initiated.

Existing methods also rely on the relevant clinician being aware that a patient could be eligible for a particular treatment or clinical trial, and in turn informing that they are eligible at a time when this information can be acted upon. This relies on the clinician both having knowledge of the particular treatment in the first place, and remembering to inform the patient at the relevant time.

The combination of these factors means that patients are often not able to enroll in a particular trial or go ahead with a particular treatment until it is too late for them to do so. From the perspective of Clinical Research Organisations, pharmaceutical companies and others offering clinical trials or particular medical treatments, existing processes often result in possibly eligible patients not being reached in time, and the pool of eligible patients being unnecessarily reduced.

In more detail, a typical existing pathway for enrolling a patient in a clinical trial may start with the patient, attending their general practitioner or family doctor with symptoms of a particular disease. The general practitioner then investigates and either establishes a diagnosis or refers them to a specialist who does so. Treatment for the disease is then initiated, possibly by a different clinician. Subsequently, and possibly only after several rounds of treatment for the disease, it may occur to a clinician that the patient could potentially be eligible for a clinical trial. The patient may then be asked whether they want to participate in the trial. However, at this late stage, it may be that a previously eligible patient is now excluded from the trial, e.g. because they have already undergone some treatment and are no longer treatment-naïve.

SUMMARY OF INVENTION

Embodiments of the disclosure aim to address the above problems and others. Aspects of the invention are as set out in the independent claims and optional features are set out in the dependent claims.

Aspects of the disclosure are set out in the independent claims and optional features are set out in the dependent claims. Aspects of the disclosure may be provided in conjunction with each other, and features of one aspect may be applied to other aspects.

One aspect of the disclosure provides a computer-implemented method of determining a medical treatment for a patient, the method comprising: obtaining, with data ingestion circuitry, a patient data set comprising a plurality of patient values each indicative of a characteristic of the patient; applying, with a model, a set of eligibility criteria to the patient values to determine whether the patient is eligible for the medical treatment; obtaining, with the data ingestion circuitry and in response to a detection that the status of the patient data has changed in an electronic medical records system, one or more further patient values for the patient; reapplying, with the machine learning model, the eligibility criteria to the patient data set to determine whether the patient is eligible for the medical treatment; obtaining, with the data ingestion circuitry and in response to a determination that a status of diagnosis data in the medical records system has changed, an indication of a diagnosis of a medical condition for the patient; and, in response to the indication that the patient has been diagnosed with the medical condition, and that the patient is eligible for the medical treatment, providing, through a user interface layer or through a network interface connection, an output signal to direct a clinician to provide the patient with the medical treatment.

The method may further comprise continually monitoring, with the data ingestion circuitry, a status of the patient data in the electronic medical records system. The method may comprise obtaining, with the data ingestion circuitry, patient values, e.g. the patient data set, at regular intervals, e.g. from the electronic medical records system. For example, the method may comprise at regular intervals, providing a request signal to the electronic medical system that is configured to cause the electronic medical records system to provide the patient values. Alternatively or additionally, the electronic medical records system itself may be configured, e.g. preprogrammed, to provide the patient data/values at the regular intervals, e.g. automatically. Alternatively or additionally, the electronic medical records system may be configured, to provide the patient data in response to a change in the patient data, e.g. the entry of new patient values.

The model may be a computer model, for example, the model may be a machine learning model. The model, e.g. machine learning model, may be trained to determine patient eligibility for the medical treatment. The model may be trained using training data. The method may further comprise training the model with training data. The training data may comprise clinical trial criteria. The clinical trial criteria may be provided e.g. by pharmaceutical companies or other institutions licensed/authorised to run clinical trials (such as biotech firms). The clinical trial criteria may also comprise diagnostic data. The training data may also comprise Electronic Medical Record (EMR) data (which may include demographic data, risk factors, medical history, presentation data, investigation results, medication history, allergies and/or genetic data etc).

Alternatively, the model may be a matching algorithm. For example, the model may determine that the patient is eligible for the medical treatment in response to one or more eligibility criteria being met. Additionally or alternatively, the model may determine that the patient is not eligible for the medical treatment in response to one or more eligibility criteria not being met.

The medical treatment may comprise enrolling the patient in a clinical trial.

The method may further comprise obtaining an indication of an outcome of a medical treatment, updating the data set to include the indicated outcome.

The method may further comprise determining an adjustment to the medical treatment, based on the indicated outcome, and providing a further output signal to direct a clinician to adjust the medical treatment.

The method may further comprise adjusting the eligibility criteria, based on the indicated outcome.

The patient values may comprise indications of physiological parameters of the patient.

Obtaining one or more further patient values for the patient may comprise providing a request to a clinician and/or the patient for one or more patient values.

Obtaining one or more further patient values for the patient may comprise obtaining an indication from a clinician of the results of a consultation with the patient.

Obtaining one or more further patient values for the patient may comprise obtaining an indication from a clinician of the results of an investigation to establish a diagnosis of the patient with the medical condition.

Obtaining one or more further patient values may comprise obtaining one or more patient values at a first time, and obtaining one or more patient values at a second time, and at each of the first time and the second time, reapplying the eligibility criteria to the patient data set to determine whether the patient is eligible for the medical treatment.

The patient values may comprise indications of physiological parameters of the patient. For example, the patient values may comprise data indicating: the medical history of the patient, signs and symptoms of disease they are currently exhibiting, risk factors such as age, gender, height, weight, smoking status. The patient values may additionally or alternatively comprise demographic data, such as geographical location data (e.g. where the patient lives), and ethnicity data. In some examples, the patient data may include genomic data relating to the patient.

The eligibility criteria may comprise a plurality of associations between one or more of the characteristics of the patient, and eligibility for the treatment. For example, each eligibility criterion may comprise a defined function which indicates a relationship between a particular characteristic and eligibility for the treatment. The machine learning model may be configured to combine the plurality of associations to determine whether the patient is eligible for the medical treatment. The eligibility criteria may correspond to characteristics of the patient, and may comprise continuous and/or discrete values associated with the patient. The eligibility criteria may include inclusion criteria, and/or exclusion criteria. Examples of eligibility criteria may include age, biological sex, comorbidities, diagnosis, treatment exposure to date, allergies etc.

The output signal may comprise a patient notification, a clinician notification (e.g. a GP notification, Consultant/other doctor notification, Principle investigator notification). The output signal may be configured to indicate that the patient is eligible for the treatment. The output signal may also be configured to provide information relating to the treatment, e.g. additional information to participate in a clinical trial (such as information about the trial or internet links to such information, contact details for enrolment in the trial).

The EMR data will be pre-processed and undergo feature extraction but these processes are yet to be fully drawn out. Dimensionality reduction may be required but this will largely be accomplished by the model itself (in terms of only looking for inclusion and exclusion criteria matching).

Obtaining a patient data set may comprise obtaining genomic data of the patient. The eligibility criteria may comprise an association between genetic information and eligibility for the medical treatment.

The medical condition may be cancer. The medical treatment may be or comprise a cancer treatment. The medical treatment may comprise enrolment in a medical trial for a cancer treatment. In other examples, the medical condition may be a non-cancer medical condition. For example, the medical treatment may be a treatment for sepsis, neurological conditions such as multiple sclerosis or Parkinson's disease, dementia, and/or cardiovascular diseases. The medical treatment may comprise enrolment in a medical trial for such treatments.

Another aspect provides a computer-implemented method of identifying eligible patients for a medical treatment, the method comprising: obtaining, with data ingestion circuitry, a patient data set comprising a plurality of patient values for each of a plurality of patients in a population, wherein the patient values are each indicative of a characteristic of the associated patient; applying, with a machine learning model trained to determine patient eligibility for a medical treatment, a set of eligibility criteria to the patient data set to determine a subset of the patients in the population that are provisionally eligible for the medical treatment; obtaining, with the data ingestion circuitry and in response to a detected change in the patient data in an electronic medical records system, one or more further patient values for one or more of the patients in the subset, and updating the patient data set based on the obtained further patient values; reapplying the eligibility criteria, with the machine learning model, to determine which of the patients in the subset are still eligible for the medical treatment based on the obtained further patient values; obtaining, with the data ingestion circuitry, an indication of a diagnosis of a medical condition for one or more patients in the subset; in response to the obtained indications of a diagnosis, providing, through a user interface layer or a network interface connection, one or more output signals to direct a clinician to provide the one or more of the patients that are eligible and for whom a diagnosis of a medical condition is obtained with the medical treatment.

Obtaining one or more further patient values for one or more of the patients in the subset may comprise providing a request to at least one of the patients and/or at least one clinician to provide one or more patient values.

Another aspect provides a computer-implemented method of determining whether a patient is eligible for a medical treatment, the method comprising: obtaining, with data ingestion circuitry, a patient data set comprising a plurality of patient values each indicative of a characteristic of the patient; applying, with a machine learning model trained to determine patient eligibility for a medical treatment, a set of eligibility criteria to the patient values to determine whether the patient is eligible for the medical treatment; prompting, through a user interface layer or a network interface connection, a clinician to provide further patient values for the patient; in response to the provided further patient values, reapplying, with the machine learning model, the set of eligibility criteria to the patient values to determine whether the patient is eligible for the medical treatment; prompting, through the user interface layer or network interface connection, a clinician to provide an indication of whether the patient has been diagnosed with a medical condition; in response to an indication that the patient has been diagnosed with the medical condition, prompting, through the user interface layer or network interface connection, the clinician to provide the patient with the medical treatment.

Another aspect of the disclosure provides a computer-implemented method of determining a medical treatment for a patient, the method comprising: obtaining, with data ingestion circuitry, a patient data set comprising a plurality of patient values each indicative of a characteristic of the patient; applying a set of eligibility criteria to the patient values to determine whether the patient is eligible for the medical treatment; obtaining, with the data ingestion circuitry and in response to a detection that the status of the patient data has changed in an electronic medical records system, one or more further patient values for the patient; reapplying the eligibility criteria to the patient data set to determine whether the patient is eligible for the medical treatment; obtaining, with the data ingestion circuitry and in response to a determination that a status of diagnosis data in the medical records system has changed, an indication of a diagnosis of a medical condition for the patient; and, in response to the indication that the patient has been diagnosed with the medical condition, and that the patient is eligible for the medical treatment, providing, through a user interface layer or through a network interface connection, an output signal to direct a clinician to provide the patient with the medical treatment.

Applying the set of eligibility criteria may comprise applying the set of eligibility criteria with a machine learning model trained to determine patient eligibility for a medical treatment. The eligibility criteria may be reapplied with the machine learning model.

Another aspect of the disclosure provides a computer-implemented method of determining a medical treatment for a patient, the method comprising: obtaining a patient data set comprising a plurality of patient values each indicative of a characteristic of the patient; applying a set of eligibility criteria to the patient values to determine whether the patient is eligible for the medical treatment; obtaining one or more further patient values for the patient and updating the patient data set based on the obtained further patient values; reapplying the eligibility criteria to the patient data set to determine whether the patient is eligible for the medical treatment; obtaining an indication of a diagnosis of a medical condition for the patient; and, in response to the indication that the patient has been diagnosed with the medical condition, and that the patient is eligible for the medical treatment, providing an output signal to direct a clinician to provide the medical treatment for the patient.

Obtaining the patient data set may comprise obtaining the patient data set with data ingestion circuitry. Applying the set of eligibility criteria may comprise applying the set of eligibility criteria with a machine learning model trained to determine patient eligibility for a medical treatment. The one or more further patient values may be obtained with the data ingestion circuitry and in response to a detection that the status of the patient data has changed in an electronic medical records system. The eligibility criteria may be reapplied with the machine learning model. The indication of a diagnosis of a medical condition for the patient may be obtained with the data ingestion circuitry, and may be obtained in response to a determination that a status of diagnosis data in the medical records system has changed. The output signal may be provided through a user interface layer or through a network interface connection.

Another aspect may provide an artificial neural network configured to perform any of the methods described.

Another aspect may provide a computer program product comprising program instructions configured to program a processor to perform any of the methods described.

BRIEF DESCRIPTION OF FIGURES

Embodiments of the disclosure will now be described in detail with reference to the accompanying drawings, in which.

In the drawings, like reference numerals are used to indicate like elements.

SPECIFIC DESCRIPTION

Described below with reference to the figures are examples of systems and methods in which the criteria by which patients are judged to be eligible for a particular medical treatment, for example as a clinical trial, are reapplied each time a patient's electronic medical records (EMR) are updated. This in turn allows for real time updates of the patient's eligibility to be provided to the relevant clinician or the patient themselves, meaning that a decision on the patient's inclusion in the trial can be reached at an earlier stage in the diagnosis and treatment pathway.

Figure 1:
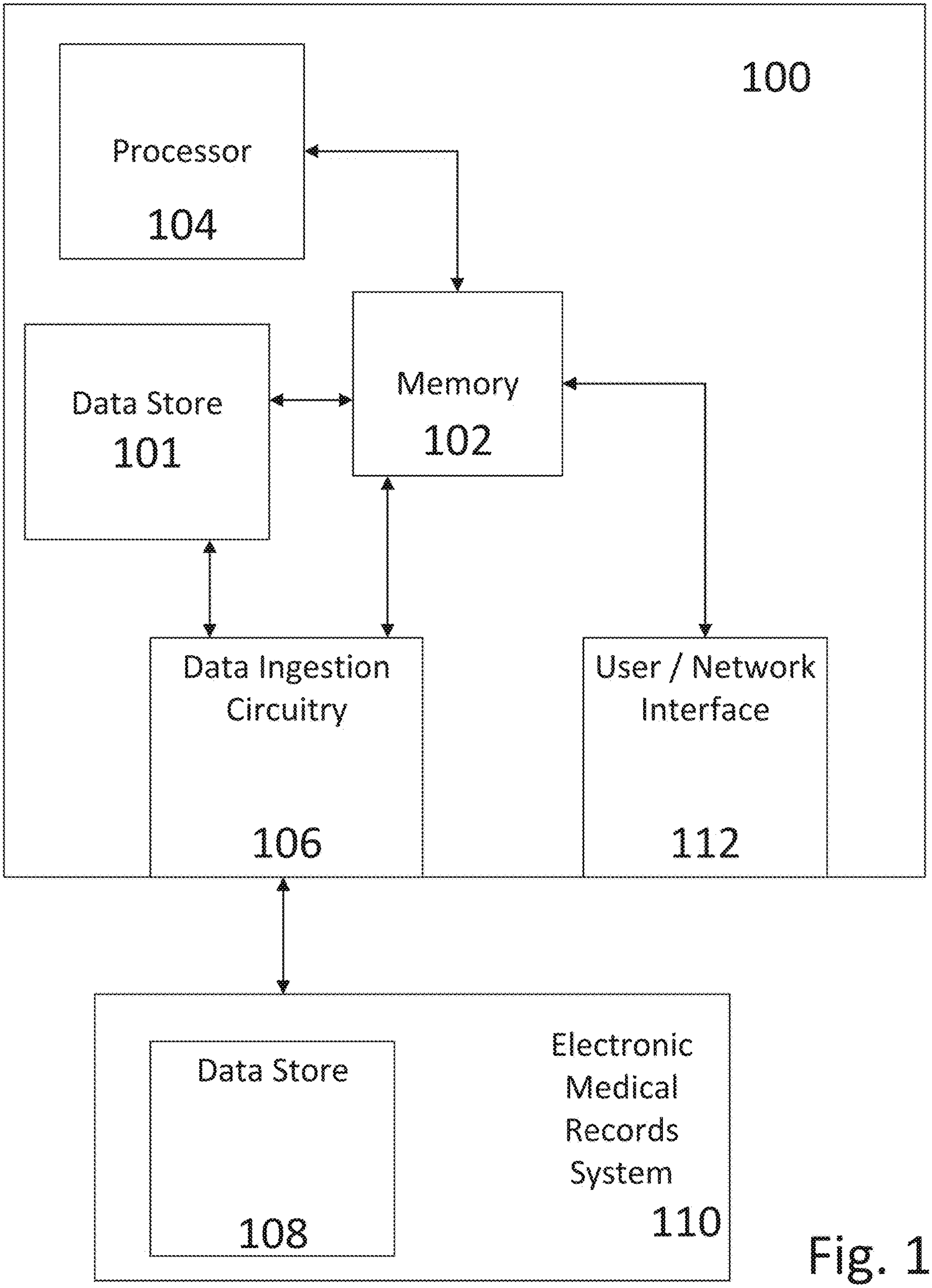
FIG. 1 illustrates an example computer system for carrying out one or more methods of determining a medical treatment or eligibility for a clinical trial for one or more patients.

FIG. 1 illustrates an example controller 100, in the form of a computer system, which is configured to determine a medical treatment and/or eligibility for a clinical trial for one or more patients. The controller 100 comprises a data store 101 configured to store data, such as patient data, as well as criteria data corresponding to a set of eligibility criteria for determining whether a patient is eligible for one or more medical treatments.

The controller 100 also comprises a processor 104, and a memory 102 that is arranged to store instructions and provide them to the processor 104 to be executed. In particular, the memory 102 may be configured to store program instructions that are configured to program the processor 104 to apply the stored eligibility criteria to the stored patient data to determine if a given patient is eligible for a medical treatment. Examples of such methods are described below, e.g. with reference to FIGS. 2 to 5. In turn, the processor is configured to execute the set of instructions and provide one or outputs of the executed method to the memory 102.

The controller 100 further comprises data ingestion circuitry 106. The ingestion circuitry 106 is configured as an input for the controller 100, and to obtain data, such as patient data, from outside of the controller 100, such as from an external device or server, to which the controller 100 may be connected, e.g. via a network. In particular, the data ingestion circuitry 106 is connected to a data store 108. The data store 108 may not form part of the controller 100 (i.e.

the computer system), and may instead be provided in an external device or server with which the controller 100 can communicate via ingestion circuitry 106, e.g. over a network (e.g. WLAN such as the internet).

The data store 108 of the electronic medical records system 110 stores patient values, i.e. data relating to characteristics of each of a plurality of patients. This data may include, for each patient, physiological data indicating characteristics of the patient such as their medical history, signs and symptoms of disease they are currently exhibiting, as well as risk factors such as their age, gender, height, weight, smoking status etc. The patient values may also include other demographic data, such as where the patient lives and their ethnicity. In some examples, the patient data may include genomic data relating to the patient. The data store 108 may be provided as part of an electronic medical records system 110, such that the data stored in the data store 108 can be updated by one or more users connected to the records system. Such users could include medical practitioners (clinicians) or the patients themselves. For example, a clinician may update the data in the data store 108 via the medical records system to record symptoms of disease that the patient is exhibiting at an appointment. The patient values which make up the data set for that patient in the data store 108 may then be further updated at each subsequent stage of a diagnosis (and/or treatment) pathway. For example, if tests or investigations are carried out in response to the symptoms exhibited, the patient data set can be updated to include the results of these tests. Similarly, if a diagnosis of a particular condition is then confirmed, the patient data set can be further updated to include an indication of the diagnosis.

The data ingestion circuitry 106 is connected to the electronic medical records system 110, e.g. via a network such as a wide area network (WAN) such as the internet, and is configured to obtain patient data from the data store 108, and for example store it in the data store 101 of the controller 100. In particular, the data ingestion circuitry 106 is configured to obtain patient data for a particular patient from the data store 108 at each stage of the pathway described above. The data ingestion circuitry 106 is coupled to at least one of the internal data store 101 and the memory 102, and is configured to provide the obtained patient data from the data store 108 to the memory 102 and/or data store 101.

The memory 102 is configured to provide instructions to the processor 104 to apply the eligibility criteria stored in the data store 101 to the obtained patient data, at each stage of the pathway (e.g. each time that the patient data is updated as described above), to determine if the patient is eligible for a particular medical treatment, e.g. a clinical trial.

These eligibility criteria may be applied to the patient values using a particular model, e.g. a machine learning model, which is configured to determine patient eligibility for the medical treatment as a function of the various parameters which each of the patient values indicate. The model may be configured to calculate a value indicating the suitability of the patient to the medical treatment based on their patient values. The memory 102 may comprise instructions for the processor 104 to implement the model. In at least some examples the mode is a machine learning model that has been previously trained to determine patient eligibility for the medical treatment. The eligibility criteria may comprise an association between each of several characteristics of the patient (which may correspond to the characteristics that the patient values indicate) and eligibility for the treatment. The model is configured to apply each of these criteria to each of the patient values for a particular patient, and calculate whether the patient is eligible.

The controller 100 further comprises a user/network interface output connection 112. The output connection 112 is connected to a network, e.g. a wide area network (WAN) such as the internet, and is configured to provide an output signal to a user's device, via the network. In some examples the output connection 112 may be connected to provide the output signal to the user device via the electronic medical records system 110. The output signal may comprise an indication that the patient is eligible for a particular medical treatment, and thus may direct a user, e.g. a clinician, to take action to provide that medical treatment to the patient.

The medical treatment described could include, or correspond to, enrolment in a clinical trial. The medical conditions described in relation to each of the FIGS. 1 to 5 could be a cancer condition, and the medical treatment could include a treatment for cancer, for example enrolment in a clinical trial for a cancer treatment. However, it will be appreciated that this is merely exemplary, and that any of the methods described could equally be applied to other types of medical conditions and treatments.

Various methods which may be performed by the controller 100 are now described in more detail with reference to FIGS. 2 to 5.

Figure 2:
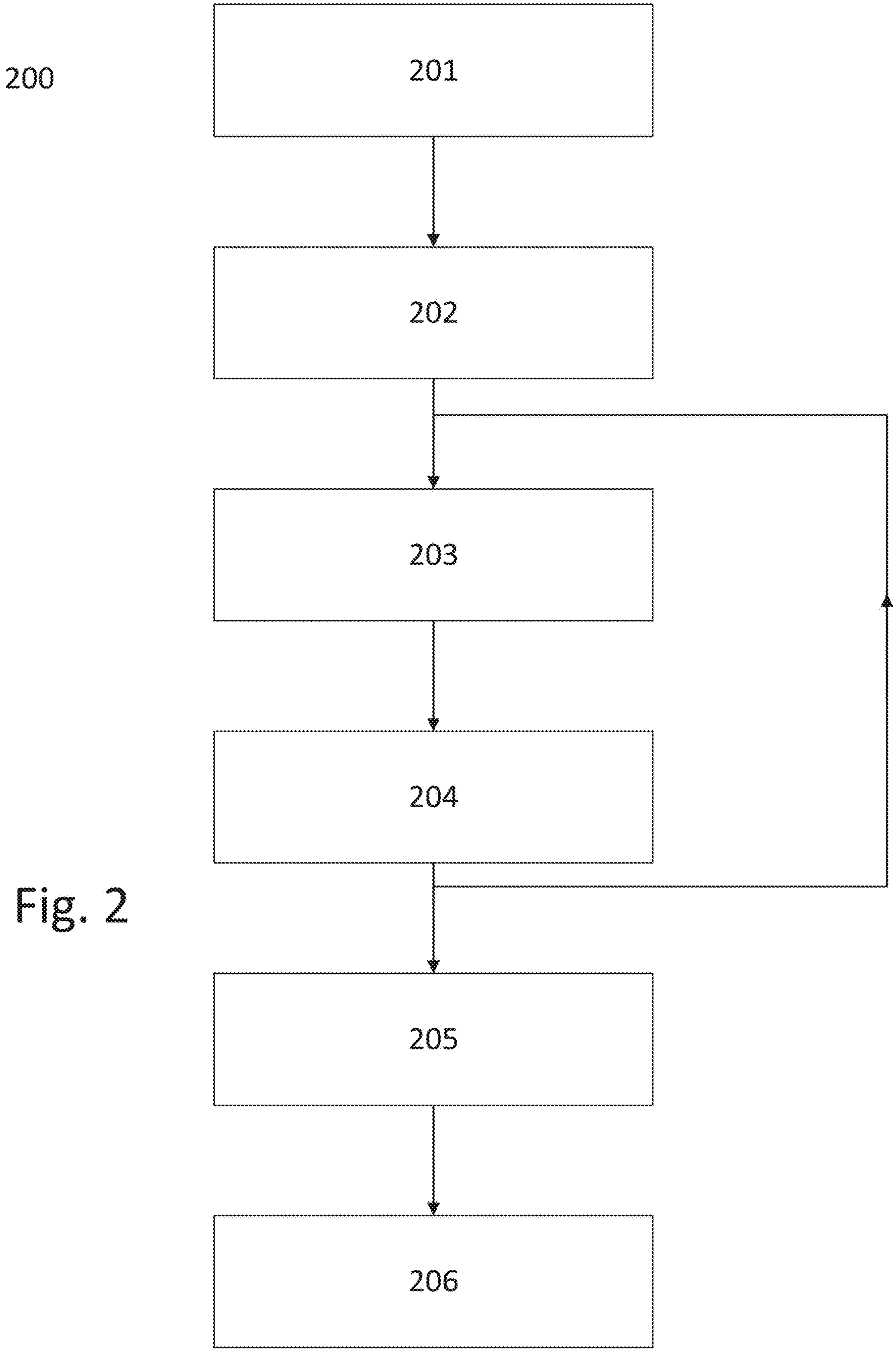
FIG. 2 is a flow chart illustrating an example method of determining a medical treatment for a patient.

FIG. 2 illustrates is a flow chart illustrating an example of a computer implemented method 200 of determining a medical treatment for a patient, and which may be performed by the apparatus shown in FIG. 1, e.g. by controller 100. In this method, at a first step 201, data ingestion circuitry, such as data ingestion circuitry 106, obtains a patient data set comprising a plurality of patient values each indicative of a characteristic of the patient, e.g. from a data store as described above. At a second step 202, a set of eligibility criteria are applied to the obtained patient values to determine whether, at that time the patient is eligible for the medical treatment. The application of the eligibility criteria may be performed using a machine learning model that has been trained to determine patient eligibility for the medical treatment.

At a third step 203, one or more further patient values for the patient are obtained, e.g. from the data store of the electronic medical records system. These further patient values may correspond to a change in the patient's data set, for example as a result of a clinician updating the data set in an electronic medical records system to indicate signs or symptoms that the patient is exhibiting at a clinical appointment/consultation. Alternatively or additionally, one or more further patient values for the patient may be obtained as an indication of the results of an investigation to establish a diagnosis of the patient with the medical condition, entered by a clinician.

At next step 204, the eligibility criteria may be reapplied to the updated patient data set, to determine whether the patient is eligible for the medical treatment.

As indicated in FIG. 2, steps 203 and 204 may repeated each time that the patient's medical record is updated. As such, the method may include obtaining one or more further patient values comprises at a first time, and obtaining one or more patient values at a second time, and at each of the first time and the second time, reapplying the eligibility criteria to the patient data set to determine whether the patient is eligible for the medical treatment. Obtaining one or more further patient values as in step 203 may include providing a request to a clinician and/or the patient themselves, prompting them to provide one or more patient values, e.g. to input such data into their device-which can be stored in the electronic records system and in turn accessed by the computer system (e.g. controller 100 via data ingestion circuitry 106).

Such further data may be obtained as a result of continually monitoring the status of the patient data in the electronic medical records system, e.g. via the data ingestion circuitry. For example, with reference to FIG. 1, the controller 100 may be configured to send request signals at regular intervals to the records system 110, via the data ingestion circuitry 106, to cause the records system 110 to provide further patient data for the patient in response to any change in the patient's data set in the data store 108. Additionally or alternatively, the electronic medical records system 110 may be configured to provide the further data to the controller 100, via data ingestion circuitry 106, automatically in response to any change in the patient data stored in the data store 108.

Subsequently, at step 205, an indication of a diagnosis of a particular medical condition may be obtained. This may be obtained for example in response to a clinician updating the data set in an electronic medical records system to indicate that the patient is diagnosed with the condition. In response to this indication, e.g. confirmation of diagnosis, at step 206, an output signal is provided, e.g. to a clinician. In particular, if at step 204 it is determined that the patient is eligible for the medical treatment then, in response to an indication of a diagnosis received at step 205, an output signal is provided that directs a clinician to provide the patient with the particular medical treatment.

As discussed above, the medical treatment described could include, or correspond to, enrolment in a clinical trial.

Although not illustrated in FIG. 2, the method 200 may include a further, later, step of obtaining an indication of the outcome of the medical treatment. For example, the electronic medical records system 110 may store, e.g. in data store 108, an indication of whether or not the treatment was successful. This information may be provided to the controller 100, via the data ingestion circuitry 106, and stored. In some examples, an adjustment to the medical treatment is then determined based on the indicated outcome, and the controller 100 may then provide a further output signal which directs a clinician to adjust the medical treatment. In some examples, the eligibility criteria that are used to determine whether a patient is eligible for the medical treatment are adjusted based on the indicated outcome, e.g. using machine learning techniques. In this way the model used to determine patient eligibility is updated and thereby may be more accurate when implemented for future patients.

Figure 3:
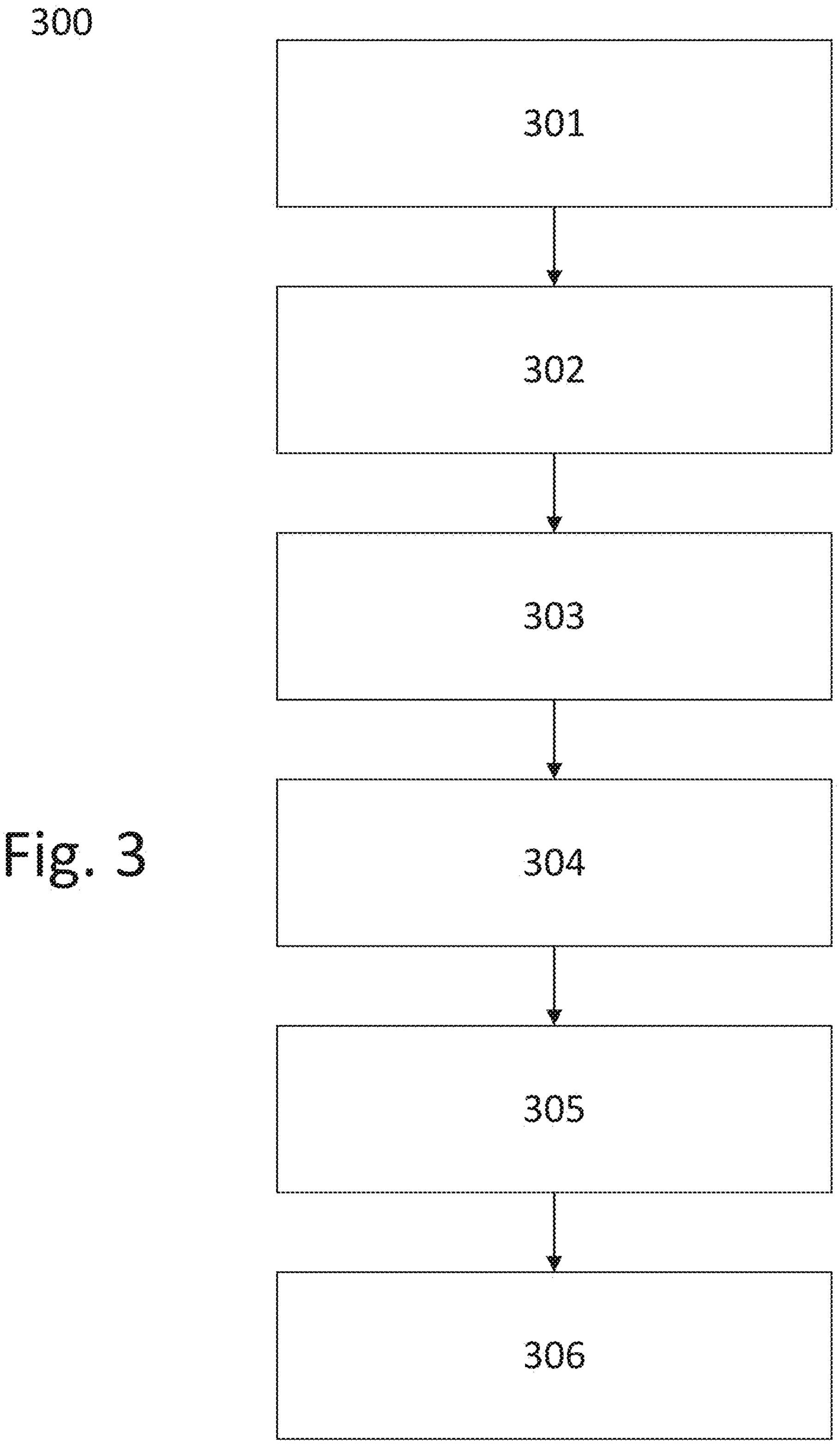
FIG. 3 is a flow chart illustrating an example method of identifying eligible patients for a medical treatment.

FIG. 3 is a flow chart illustrating an example of a different computer implemented method 300, which is a method of identifying eligible patients for a particular medical treatment (or clinical trial), and which may be performed by the apparatus shown in FIG. 1, e.g. by controller 100. For example, whilst the method 200 described above with reference to FIG. 2 may determine a medical treatment for a single patient, the method 300 may identify which out of a plurality of patients in a given patient population are eligible for a particular treatment.

At a first step 301, data ingestion circuitry obtains a patient data set comprising a plurality of patient values for each of a plurality of patients in a population. The patient values are each indicative of a characteristic of the associated patient, such as the characteristics discussed above. At second step 302, a set of eligibility criteria are applied to the patient data set to determine a subset of the patients in the population that are provisionally eligible for the medical treatment. The application of the eligibility criteria may be performed using a machine learning model that has been trained to determine patient eligibility for the medical treatment. As a result, a subset of the patients in the population may be determined to be provisionally eligible for the medical treatment. At step 303, the data ingestion circuitry obtains, in response to a detected change to the patient data, e.g. in an electronic medical records system, one or more further patient values for one or more of the patients in the subset, and updating the patient data set based on the obtained further patient values. The further patient values may correspond to a change in the patient's data set, for example as one or more of the patients or their clinicians updating the data set in an electronic medical records system to indicate signs or symptoms that the patients are exhibiting. At subsequent step 304, the eligibility criteria are reapplied to the updated patient values (which are based on the obtained further patient values) for each of the patients in the subset, e.g. with the machine learning model, to determine which of the patients in the subset are still eligible for the medical treatment.

Subsequently, at step 305, an indication of a diagnosis of a particular medical condition may be obtained for one or more of the patients in the subset which are determined to still be eligible at step 304. This may be obtained for example in the same way as described above in relation to FIG. 2 step 205. At step 306, in response to the obtained indications of a diagnosis, one or more output signals are provided, for each of the patients that are diagnosed with the condition, and which are determined to still be eligible for the medical treatment. The output signals each direct a clinician to provide each of these patients with the medical treatment, for example by enrolling them in a clinical trial.

It will be appreciated that each of the steps of method 300 may occur at different times for each of the patients in the population, and that therefore the method 300 may not progress linearly or sequentially across the entire population. For example, whilst steps 301 to 306 may progress as a linear sequence for each individual patient, this sequence may take place at different times for each patient.

Figure 4:
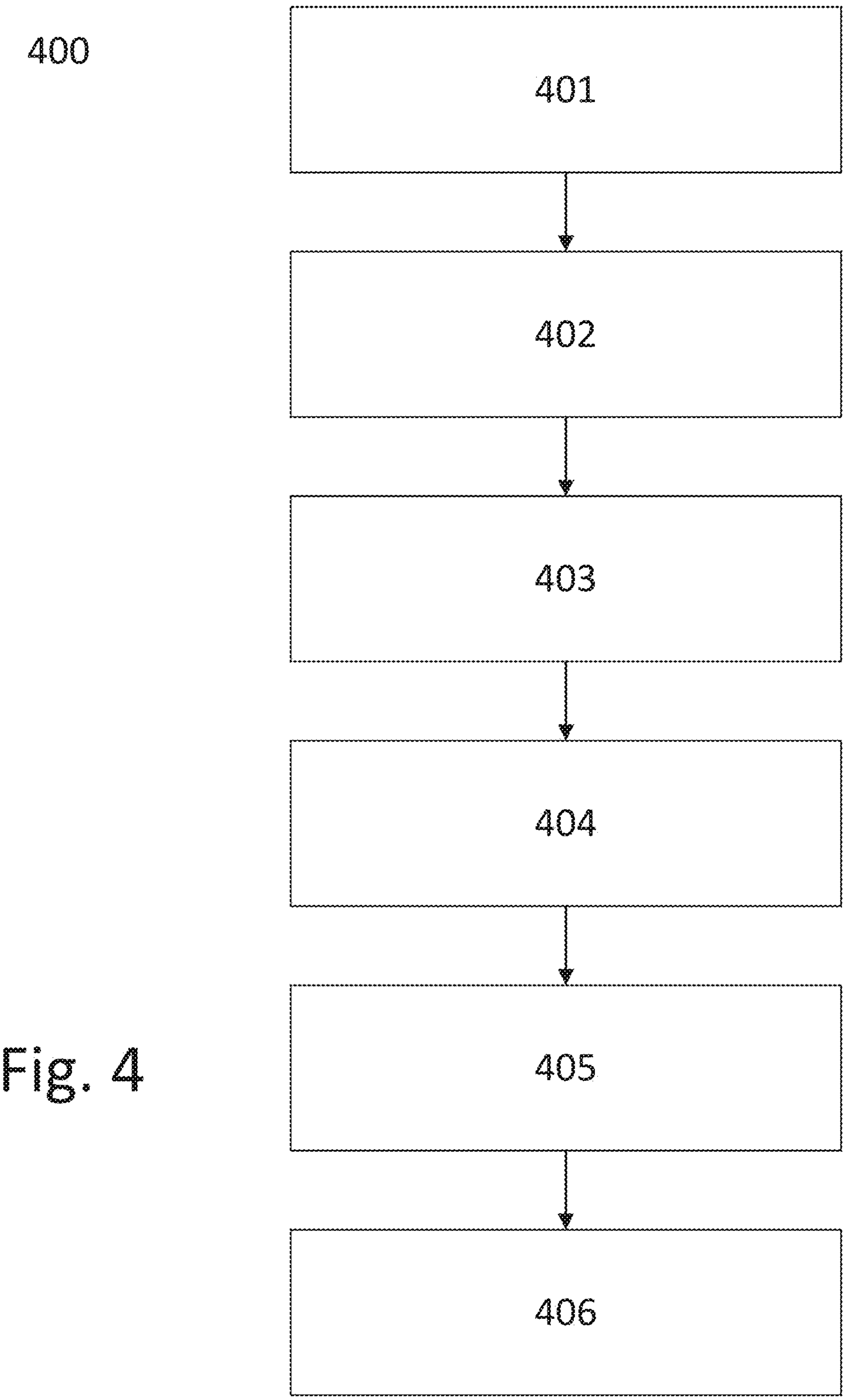
FIG. 4 is a flow chart illustrating an example method of determining whether a patient is eligible for a medical treatment.

FIG. 4 is a flow chart illustrating an example a computer implemented method 400 of determining whether a patient is eligible for a medical treatment, and may be performed by the apparatus shown in FIG. 1, e.g. by controller 100. The method comprises at a first step 401, obtaining, with data ingestion circuitry, a patient data set comprising a plurality of patient values each indicative of a characteristic of that patient—e.g. the patient values discussed above. At the next step 402, a set of eligibility criteria to the patient values to determine whether the patient is eligible for the medical treatment, using a machine learning model trained to determine patient eligibility for a medical treatment, e.g. as described above.

At next step 403, a clinician is prompted provide further patient values for the patient. This step is performed using a user interface layer or a network interface connection, such as the output connection 112 described above in relation to FIG. 1. Step 403 can include outputting a signal to the user, e.g. clinician, so that on their device they are prompted to assess the patient and provide further patient values relating to particular characteristics. For example, if a particular patient has been determined, at step 402, to be eligible for the medical treatment, then in the event they attend a medical appointment, e.g. with their GP/family doctor, the doctor may be prompted to provide further patient values. Such further patient values may correspond for example to the signs and symptoms of disease they are exhibiting, or lifestyle characteristics. The prompt may be provided via a network to which both a computer system providing the prompt (e.g. controller 100) and the clinician's device are connected, and may be presented to the clinician on that device, e.g. in the form of a reminder or interface/form into which the clinician can enter the further patient values.

In response to the further patient values which have been provided, the method further comprises, at step 404, reapplying, with the machine learning model, the set of eligibility criteria to the patient values to determine whether the patient is eligible for the medical treatment. At subsequent step 405, a clinician is prompted to provide an indication of whether the patient has been diagnosed with a medical condition. Such a prompt may be provided in the same or similar way to the prompt described above at step 403, and may only be provided in the event that it is determined at step 404 that the patient is still eligible for the medical treatment. At final step 406, in response to an indication that the patient has been diagnosed with a medical condition, the clinician is prompted to provide the medical treatment for the eligible patient. As discussed above, the medical treatment may comprise enrolment in a clinical trial, and the prompt may prompt the clinician to offer to the patient that they enrol in the clinical trial. It will be appreciated that the "clinician" described in relation to method 400 may correspond to a single person, or may correspond to different clinicians at each of the steps described above, who have become involved in the patient's care at different stages.

Although not shown in FIG. 4, it will be appreciated that in some examples, one or more additional rounds of prompting the clinician to provide patient data, and determining eligibility may be included. For example, at an intermediate stage a clinician may be prompted to provide further patient data, such as the outcome of tests or investigations prior to a diagnosis being established. Such additional intermediate steps may be provided for example between step 404 and step 405 shown in FIG. 4.

In other examples, one or more of the "prompting" steps described above may be directed to the patient themselves, rather than their clinician.

Figure 5:
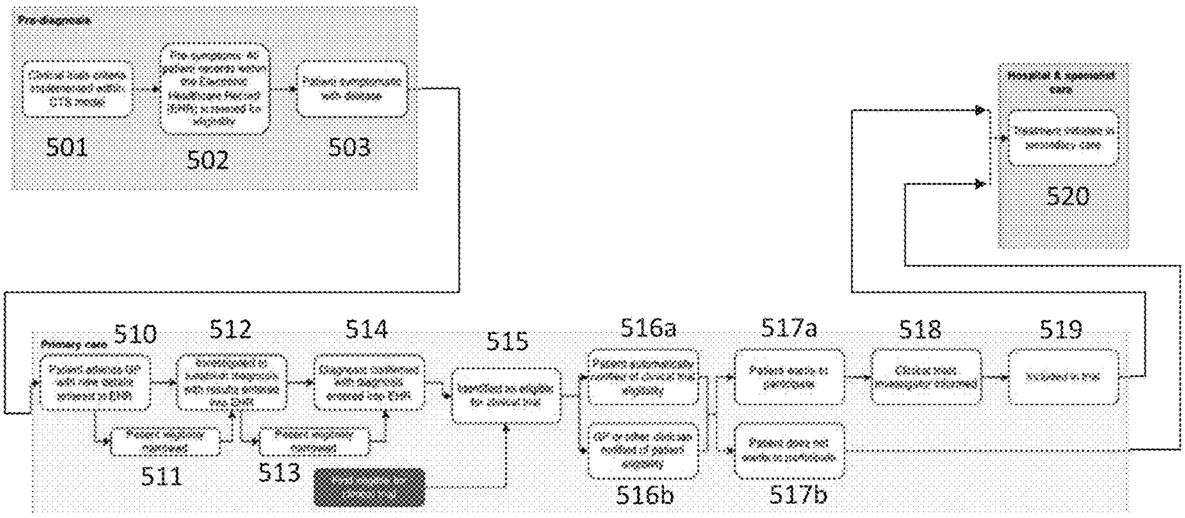
FIG. 5 is a flow chart illustrating an example method for determining whether a patient is eligible for a clinical trial.

FIG. 5 illustrates an example 500 of an individual patient's diagnosis and treatment timeline, incorporating methods of determining their eligibility for a clinical trial, including steps such as those described above with reference to FIGS. 2 to 4.

The first step 501 of the process 500 includes, at a pre-diagnosis phase, implementing clinical trials criteria within a machine learning model. This step may correspond to inputting into the model the particular criteria by which it will be determined whether patients are eligible for the clinical trial, e.g. as a function of the various parameters represented by the patient values described above. At step 502, all patient records that are stored within a particular electronic healthcare record (EHR) are screened for eligibility—i.e. eligibility for the clinical trial. At step 503, a particular one of the patients whose records are stored in the EHR becomes symptomatic with the disease to which the clinical trial may relate.

At subsequent step 510, in the primary care phase, the symptomatic patient attends a GP appointment, and additional details are entered into the EHR such as details relating to their symptoms. At step 511 the patient eligibility is narrowed, by the model, based on the new details entered into the EHR. For example, the machine learning model may reapply the eligibility criteria based on the new details entered, as described above in relation to the earlier figures. In particular, it will be appreciated that step 511 may correspond to or include steps 203 and 204 of the method 200, steps 303 and 304 of the method 300, and/or step 404 of the method 400. At step 512, investigations are carried out to establish a diagnosis, with the results of these investigations entered into the EHR.

At step 513, patient eligibility is again narrowed based on the results of the investigations, by the model reapplying the eligibility criteria. In particular, it will be appreciated that step 511 may correspond to or include the reapplication of steps 203 and 204 in the method 200, and/or additional steps of obtaining patient data and reapplying eligibility criteria as described above in relation to steps 303 and 304 of the method 300, and/or step 404 of the method 400. At step 514 the diagnosis is confirmed and is entered into the EHR. At step 515, the patient, if eligible and having a confirmed diagnosis, is then identified as eligible for the clinical trial. At the next stage, the patient is either automatically notified of their eligibility themselves (step 516*a*), or a GP or other clinician is notified of their eligibility (516*b*). The patient then decides whether or not they want to participate in the trial. In the event that they do not (517*b*), they proceed to hospital and specialist care 520, where treatment is initiated without enrolment into the clinical trial.

In the event that the patient wants to participate in the clinical trial 517*a*, a clinical trials investigator is informed 518, e.g. by the clinician, and the patient is then included in the trial 519. Treatment in accordance with the clinical trial is then initiated in secondary care 520.

It will be appreciated from the discussion above that the embodiments shown in the figures are merely exemplary, and include features which may be generalised, removed or replaced as described herein and as set out in the claims. For example, although the controller 100 is described as including separate a data ingestion circuitry 106 and user/network interface 112, it will be appreciated that the function of these elements could be provided by a single component, such as any suitable input/output port.

In addition, it will be appreciated that the controller 100 need not include a separate data store 101 and memory 102, and that in some examples a single memory element may be provided which both stores the patient data and/or eligibility criteria and provides instructions to the processor.

Each of the models described above may be a machine learning model, and/or may be implemented using an artificial neural network.

As used in this specification and the appended claims, the terms "machine learning," "machine learning techniques," "machine learning operation," and "machine learning model" may generally refer to any system or analytical or statistical procedure that may progressively improve computer performance of a task. In some cases, ML may generally involve identifying and recognizing patterns in existing data in order to facilitate making predictions for subsequent data. ML may include a ML model (which may include, for example, a ML algorithm). Machine learning, whether analytical or statistical in nature, may provide deductive or abductive inference based on real or simulated data. The ML model may be a trained model. ML techniques may comprise one or more supervised, semi-supervised, self-supervised, or unsupervised ML techniques. For example, an ML model may be a trained model that is trained through supervised learning (e.g., various parameters are determined as weights or scaling factors). ML may comprise one or more of regression analysis, regularization, classification, dimensionality reduction, ensemble learning, meta learning, association rule learning, cluster analysis, anomaly detection, deep learning, or ultra-deep learning. ML may comprise, but is not limited to: k-means, k-means clustering, k-nearest neighbors, learning vector quantization, linear regression, non-linear regression, least squares regression, partial least squares regression, logistic regression, stepwise regression, multivariate adaptive regression splines, ridge regression, principal component regression, least absolute shrinkage and selection operation (LASSO), least angle regression, canonical correlation analysis, factor analysis, independent component analysis, linear discriminant analysis, multidimensional scaling, non-negative matrix factorization, principal components analysis, principal coordinates analysis, projection pursuit, Sammon mapping, t-distributed stochastic neighbor embedding, AdaBoosting, boosting, gradient boosting, bootstrap aggregation, ensemble averaging, decision trees, conditional decision trees, boosted decision trees, gradient boosted decision trees, random forests, stacked generalization, Bayesian networks, Bayesian belief networks, naïve Bayes, Gaussian naïve Bayes, multinomial naïve Bayes, hidden Markov models, hierarchical hidden Markov models, support vector machines, encoders, decoders, auto-encoders, stacked auto-encoders, perceptrons, multi-layer perceptrons, artificial neural networks, feedforward neural networks, convolutional neural networks, recurrent neural networks, long short-term memory, deep belief networks, deep Boltzmann machines, deep convolutional neural networks, deep recurrent neural networks, or generative adversarial networks.

The hardware logic configurable to implement a described herein may be embodied in hardware on an integrated circuit. Generally, any of the functions, methods, techniques or components described above can be implemented in software, firmware, hardware (e.g., fixed logic circuitry), or any combination thereof. The terms "module," "functionality," "component", "element", "unit", "block" and "logic" may be used herein to generally represent software, firmware, hardware, or any combination thereof. In the case of a software implementation, the module, functionality, component, element, unit, block or logic represents program code that performs the specified tasks when executed on a processor. The algorithms and methods described herein could be performed by one or more processors executing code that causes the processor(s) to perform the algorithms/methods. Examples of a computer-readable storage medium include a random-access memory (RAM), read-only memory (ROM), an optical disc, flash memory, hard disk memory, and other memory devices that may use magnetic, optical, and other techniques to store instructions or other data and that can be accessed by a machine.

The terms computer program code and computer readable instructions as used herein refer to any kind of executable code for processors, including code expressed in a machine language, an interpreted language or a scripting language. Executable code includes binary code, machine code, bytecode, code defining an integrated circuit (such as a hardware description language or netlist), and code expressed in a programming language code such as C, Java or OpenCL. Executable code may be, for example, any kind of software, firmware, script, module or library which, when suitably executed, processed, interpreted, compiled, executed at a virtual machine or other software environment, cause a processor of the computer system at which the executable code is supported to perform the tasks specified by the code.

A processor, computer, or computer system may be any kind of device, machine or dedicated circuit, or collection or portion thereof, with processing capability such that it can execute instructions. A processor may be any kind of general purpose or dedicated processor, such as a CPU, GPU, System-on-chip, state machine, media processor, an application-specific integrated circuit (ASIC), a programmable logic array, a field-programmable gate array (FPGA), or the like. A computer or computer system may comprise one or more processors.

It is also intended to encompass software which defines a configuration of hardware as described herein, such as HDL (hardware description language) software, as is used for designing integrated circuits, or for configuring programmable chips, to carry out desired functions. That is, there may be provided a computer readable storage medium having encoded thereon computer readable program code in the form of an integrated circuit definition dataset that when processed (i.e. run) in an integrated circuit manufacturing system configures the system to manufacture hardware logic configurable to implement a NN (e.g. NN accelerator) described herein. An integrated circuit definition dataset may be, for example, an integrated circuit description.

Training the ML model may include, in some cases, selecting one or more untrained data models to train using a training data set. The selected untrained data models may include any type of untrained ML models for supervised, semi-supervised, self-supervised, unsupervised machine learning, and/or transfer learning. The selected untrained data models may be specified based upon input (e.g., user input) specifying relevant parameters, as described elsewhere herein, to use as predicted variables or other variables to use as potential explanatory variables. For example, the selected untrained data models may be specified to generate an output (e.g., a prediction) based upon the input. Conditions for training the ML model from the selected untrained data models may likewise be selected, such as limits on the ML model complexity or limits on the ML model refinement past a certain point. The ML model may be trained (e.g., via a computer system such as a server) using the training data set. In some cases, a first subset of the training data set may be selected to train the ML model. The selected untrained data models may then be trained on the first subset of training data set using appropriate ML techniques, based upon the type of ML model selected and any conditions specified for training the ML model. In some cases, due to the processing power requirements of training the ML model, the selected untrained data models may be trained using additional computing resources (e.g., cloud computing resources). Such training may continue, in some cases, until at least one aspect of the ML model is validated and meets selection criteria to be used as a predictive model.

In some cases, one or more aspects of the ML model may be validated using a second subset of the training data set (e.g., distinct from the first subset of the training data set) to determine accuracy and robustness of the ML model. Such validation may include applying the ML model to the second subset of the training data set to make predictions derived from the second subset of the training data. The ML model may then be evaluated to determine whether performance is sufficient based upon the derived predictions. The sufficiency criteria applied to the ML model may vary depending upon the size of the training data set available for training, the performance of previous iterations of trained models, or user-specified performance requirements. If the ML model does not achieve sufficient performance, additional training may be performed. Additional training may include refinement of the ML model or retraining on a different first subset of the training dataset, after which the new ML model may again be validated and assessed. When the ML model has achieved sufficient performance, in some cases, the ML may be stored for present or future use. The ML model may be stored as sets of parameter values or weights for analysis of further input (e.g., further relevant parameters to use as further predicted variables, further explanatory variables, further user interaction data, etc.), which may also include analysis logic or indications of model validity in some instances. In some cases, a plurality of ML models may be stored for generating predictions under different sets of input data conditions. In some embodiments, the ML model may be stored in a database (e.g., associated with a server).

It will be appreciated from the discussion above that the embodiments shown in the figures are merely exemplary, and include features which may be generalised, removed or replaced as described herein and as set out in the claims. With reference to the drawings in general, it will be appreciated that schematic functional block diagrams are used to indicate functionality of systems and apparatus described herein. In addition the processing functionality may also be provided by devices which are supported by an electronic device. It will be appreciated however that the functionality need not be divided in this way, and should not be taken to imply any particular structure of hardware other than that described and claimed below. The function of one or more of the elements shown in the drawings may be further subdivided, and/or distributed throughout apparatus of the disclosure. In some embodiments the function of one or more elements shown in the drawings may be integrated into a single functional unit.

As will be appreciated by the skilled reader in the context of the present disclosure, each of the examples described herein may be implemented in a variety of different ways. Any feature of any aspects of the disclosure may be combined with any of the other aspects of the disclosure. For example method aspects may be combined with apparatus aspects, and features described with reference to the operation of particular elements of apparatus may be provided in methods which do not use those particular types of apparatus. In addition, each of the features of each of the embodiments is intended to be separable from the features which it is described in combination with, unless it is expressly stated that some other feature is essential to its operation. Each of these separable features may of course be combined with any of the other features of the embodiment in which it is described, or with any of the other features or combination of features of any of the other embodiments described herein. Furthermore, equivalents and modifications not described above may also be employed without departing from the invention.

Certain features of the methods described herein may be implemented in hardware, and one or more functions of the apparatus may be implemented in method steps. It will also be appreciated in the context of the present disclosure that the methods described herein need not be performed in the order in which they are described, or necessarily in the order in which they are depicted in the drawings. Accordingly, aspects of the disclosure which are described with reference to products or apparatus are also intended to be implemented as methods and vice versa. The methods described herein may be implemented in computer programs, or in hardware or in any combination thereof.

In some examples a controller may be provided, such as controller 100, which for example may include a general-purpose processor. The controller may be configured to perform a method according to any one of those described herein. In some examples the controller may comprise digital logic, such as field programmable gate arrays, FPGA, application specific integrated circuits, ASIC, a digital signal processor, DSP, or by any other appropriate hardware. In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein. The controller may comprise an analogue control circuit which provides at least a part of this control functionality. An embodiment provides an analogue control circuit configured to perform any one or more of the methods described herein.

Software in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, the ordering of various steps described herein may be changed, combined into composite steps, and/or separated into sub-steps to provide features described herein.

In some examples, one or more memory elements can store data and/or program instructions used to implement the operations described herein. Embodiments of the disclosure provide tangible, non-transitory storage media comprising program instructions operable to program a processor to perform any one or more of the methods described and/or claimed herein and/or to provide data processing apparatus as described and/or claimed herein.

In various embodiments of the present disclosure, execution of instruction sequences to practice the present disclosure may be performed by a computer system. In various other embodiments of the present disclosure, a plurality of computer systems 600 coupled by a communication link to a network (e.g., such as a LAN, WLAN, PTSN, and/or various other wired or wireless networks, including telecommunications, mobile, and cellular phone networks) may perform instruction sequences to practice the present disclosure in coordination with one another.

Other examples and variations of the disclosure will be apparent to the skilled addressee in the context of the present disclosure.

The invention claimed is:

1. A computer-implemented method of determining a medical treatment of a medical condition for a patient, the method comprising:

obtaining, with data ingestion circuitry, an initial patient data set comprising a plurality of patient values indicative of characteristics of the patient;

processing the initial patient data set with a neural network trained to determine patient eligibility for the medical treatment for the medical condition based on a set of eligibility criteria, said set of eligibility criteria comprising associations between the characteristics and eligibility for the medical treatment, to make an initial provisional determination that the patient is eligible for the medical treatment independent of the patient's diagnosis of the medical condition in the set of eligibility criteria, wherein the neural network has been trained, using a set of training data comprising patient characteristics and data indicative of patient eligibility for the medical treatment, to predict patient eligibility for the medical treatment from patient characteristics, and wherein the patient characteristics comprise electronic medical record data comprising one or more of: demographic data, risk factors, medical history, presentation data, investigation results, medication history, allergies, and genetic data;

obtaining, with the data ingestion circuitry and in response to a detection that a status of patient data has changed in an electronic medical records system, an updated patient data set comprising one or more further patient values for the patient;

processing the updated patient data set with the neural network to make an updated provisional determination that the patient is eligible for the medical treatment independent of the patient's diagnosis of the medical condition in the set of eligibility criteria;

obtaining, (i) with the data ingestion circuitry, (ii) in response to a detection that a status of diagnosis data has changed in the electronic medical records system, and (iii) subsequent to the updated provisional determination that the patient is eligible for the medical treatment, an indication of a diagnosis of the medical condition for the patient; and based on (i) the updated provisional determination that the patient is eligible for the medical treatment and (ii) the indication of the diagnosis of the medical condition for the patient, generating a notification of eligibility of the patient for the medical treatment and transmitting said notification through a user interface layer or through a network interface connection to:

the patient; and/or a clinician associated with the patient.

2. The method of claim 1, further comprising continually monitoring, with the data ingestion circuitry, a status of the patient data in the electronic medical records system.

3. The method of claim 1, wherein the medical treatment comprises enrolling the patient in a clinical trial.

4. The method of claim 1, further comprising obtaining an indication of an outcome of a medical treatment.

5. The method of claim 4, further comprising determining an adjustment to the medical treatment, based on the indicated outcome, and providing a further output signal to direct a clinician to adjust the medical treatment.

6. The method of claim 4, further comprising adjusting the eligibility criteria, based on the indicated outcome.

7. The method of claim 1, wherein the patient values comprise indications of physiological parameters of the patient.

8. The method of claim 1, wherein obtaining one or more further patient values for the patient comprises providing a request to a clinician and/or the patient for one or more patient values.

9. The method of claim 1, wherein obtaining one or more further patient values for the patient comprises obtaining an indication from a clinician of results of a consultation with the patient.

10. The method of claim 1, wherein obtaining one or more further patient values for the patient comprises obtaining an indication from a clinician of results of an investigation to establish a diagnosis of the patient with the medical condition.

11. The method of claim 1, wherein obtaining one or more further patient values comprises obtaining one or more patient values at a first time, and obtaining one or more patient values at a second time, and at each of the first time and the second time, reapplying the eligibility criteria to the patient data set to determine whether the patient is eligible for the medical treatment.

12. The method of claim 1, wherein obtaining a patient data set comprises obtaining genomic data of the patient, wherein the eligibility criteria comprise an association between genetic information and eligibility for the medical treatment.

13. A computer-implemented method of identifying eligible patients for a medical treatment of a medical condition, the method comprising:

obtaining, with data ingestion circuitry, an initial patient data set comprising a plurality of patient values for a plurality of patients in a population, wherein the patient values are indicative of characteristics of an associated patient;

processing the initial patient data set with a neural network trained to determine patient eligibility for the medical treatment for the medical condition based on a set of eligibility criteria, said set of eligibility criteria comprising associations between the characteristics and eligibility for the medical treatment, to determine an initial subset of the patients in the population that are provisionally eligible for the medical treatment independent of the initial subset's diagnosis of the medical condition in the set of eligibility criteria, wherein the neural network has been trained, using a set of training data comprising patient characteristics and data indicative of patient eligibility for the medical treatment, to predict patient eligibility for the medical treatment from patient characteristics, and wherein the patient characteristics comprise electronic medical record data comprising one or more of: demographic data, risk factors, medical history, presentation data, investigation results, medication history, allergies, and genetic data;

obtaining, with the data ingestion circuitry and in response to a detected change in the patient data in an electronic medical records system, an updated patient data set comprising one or more further patient values for one or more of the patients in the initial subset;

processing the updated patient data set with the neural network to determine an updated subset of the patients in the initial subset that are still eligible for the medical treatment based on the updated patient data set independent of the updated subset's diagnosis of the medical condition in the set of eligibility criteria;

obtaining, (i) with the data ingestion circuitry and (ii) subsequent to determining the updated subset, an indication of a diagnosis of the medical condition for at least one patient in the updated subset, the at least one patient defining a diagnosed subset of the patients in the updated subset; and in response to the indication, generating at least one notification of eligibility of patients in the diagnosed subset for the medical treatment and transmitting said at least one notification through a user interface layer or a network interface connection to:

the patients in the diagnosed subset; and/or at least one clinician associated with the patients in the diagnosed subset.

14. The method of claim 13, wherein obtaining one or more further patient values for one or more of the patients in the subset comprises providing a request to at least one of the patients and/or at least one clinician to provide one or more patient values.

15. The method of claim 13, wherein the medical treatment comprises enrolment in a clinical trial.

16. The method of claim 13, wherein the patient values comprise indications of physiological parameters of the patient.

17. A computer-implemented method of determining whether a patient is eligible for a medical treatment of a medical condition, the method comprising:

obtaining, with data ingestion circuitry, an initial patient data set comprising a plurality of patient values indicative of characteristics of the patient;

processing the initial patient data set with a neural network trained to determine patient eligibility for the medical treatment for the medical condition based on a set of eligibility criteria, said set of eligibility criteria comprising associations between the characteristics and eligibility for the medical treatment, to make an initial provisional determination that the patient is eligible for the medical treatment independent of the patient's diagnosis of the medical condition in the set of eligibility criteria, wherein the neural network has been trained, using a set of training data comprising patient characteristics and data indicative of patient eligibility for the medical treatment, to predict patient eligibility for the medical treatment from patient characteristics, and wherein the patient characteristics comprise electronic medical record data comprising one or more of: demographic data, risk factors, medical history, presentation data, investigation results, medication history, allergies, and genetic data;

prompting, through a user interface layer or a network interface connection, at least one clinician to provide further patient values for the patient;

obtaining, with the data ingestion circuitry, an updated patient data set comprising the further patient values;

processing the updated patient data set with the neural network to make an updated provisional determination that the patient is eligible for the medical treatment independent of the patient's diagnosis of the medical condition in the set of eligibility criteria;

prompting, (i) through the user interface layer or the network interface connection and (ii) subsequent to the updated provisional determination that the patient is eligible for the medical treatment, the at least one clinician to provide an indication that the patient has been diagnosed with the medical condition; and based on (i) the updated provisional determination that the patient is eligible for the medical treatment and (ii) the indication that the patient has been diagnosed with the medical condition, prompting, through the user interface layer or the network interface connection, the clinician to provide the patient with the medical treatment.

18. One or more machine-readable storage media comprising a plurality of instructions stored thereon that, in response to being executed, cause a processor to perform the method of claim 1.

* * * * *